United States Patent [19]

Muroki

[11] Patent Number: 5,772,688
[45] Date of Patent: Jun. 30, 1998

[54] SKIN-CONTACT TYPE MEDICAL TREATMENT APPARATUS

[75] Inventor: Masahisa Muroki, Kanazawa, Japan

[73] Assignee: Polytronics, Ltd., Kanazawa, Japan

[21] Appl. No.: 667,812

[22] Filed: Jun. 20, 1996

[51] Int. Cl.$^6$ ........................................ A61N 1/30
[52] U.S. Cl. ................... 607/1; 604/250; 128/639
[58] Field of Search ............................. 604/20; 128/640, 128/639, 641; 607/152, 2, 1

[56] References Cited

U.S. PATENT DOCUMENTS

| | | | |
|---|---|---|---|
| 4,292,968 | 10/1981 | Ellis | ................................ 604/20 |
| 5,053,248 | 10/1991 | Hakamata et al. . | |
| 5,376,107 | 12/1994 | Inagi et al. | ................... 607/152 |

FOREIGN PATENT DOCUMENTS

| | | |
|---|---|---|
| B-26 516 726 | 6/1981 | Australia . |
| 0 296 248 | 12/1988 | European Pat. Off. . |
| 1 954 431 | 5/1971 | Germany . |
| 33 09 841 | 5/1984 | Germany . |
| 61-177657 | 11/1986 | Japan . |
| 61-55979 | 11/1986 | Japan . |
| 61-55980 | 11/1986 | Japan . |
| 62-32944 | 7/1987 | Japan . |
| 2-39268 | 9/1990 | Japan . |

*Primary Examiner*—William E. Kamm
*Assistant Examiner*—Scott M. Getzow
*Attorney, Agent, or Firm*—Frishauf, Holtz, Goodman, Langer & Chick, P.C.

[57] ABSTRACT

A skin-contact type medical treatment apparatus is provided which includes: a first conductive member having a first skin-contact surface in contact with a first surface of skin when in use, the first skin-contact surface being made of metal or its alloy; and a second conductive member having a second skin-contact surface in contact with a second surface of skin different from the first surface when in use together with the first conductive member, the second skin-contact surface being made of n-type semiconductor material having a standard single electrode potential lower than that of the first skin-contact surface. The first and second conductive members are electrically connected by a protective resistor at an area different from the first and second skin-contact surfaces, the protective resistor having a resistance value in the range of from 0.1 to 50 MΩ.

13 Claims, 5 Drawing Sheets

SKIN-CONTACT TYPE MEDICAL TREATMENT APPARATUS

BACKGROUND OF THE INVENTION a) Field of the Invention

The present invention relates to a skin-contact type medical treatment apparatus particularly effective for remedying unidentified complaint syndrome such as shoulder stiffness and waist pains.

b) Description of the Related Art

With recent change in life styles and increase in elders, patients suffering from chronic body stiffness or pains are increasing in number. The main causes of these diseases are generally said to be local fatigue of muscles or nerves.

Causes which bring about fatigue of muscles and nerves differ from one person to another, and the degree of fatigue also varies. If fatigue is not temporal, such as muscle fatigue caused by sports, but is caused by usual daily life, it may lead to chronic disease. If stiffness or pains are acute, remedy must rely on physical treatment or acupuncture/moxibustion treatment at hospital. Even if stiffness or pains are relatively minor, a patient feels uncomfortable (has unidentified complaint) in daily life, and simple treatments have long been desired.

Household treatment apparatus or methods for stiffness or pains conventionally developed and commercially available include pap medicament, indirect moxibustion, metal grains, magnetic treatment apparatus, low frequency treatment apparatus, and other apparatus and methods. These all have been developed aiming at enhancing blood circulation in and out of an affected part to thereby purify locally stagnant effete material.

Of theses, the pap medicament, indirect moxibustion, and magnetic treatment apparatus seek for the effects of blood vessel dilation, the low frequency treatment apparatus seeks for the physical treatment effects of regular muscle tonus and relaxation, and the metal grains seek for the treatment through meridian and acupuncture points of Oriental medicine.

The present inventor has developed ion permeating devices (Japanese Patent No. 1388949, 1427360, and 1631137, and Japanese Utility Model Registration No. 1922166, and etc.) capable of remedying fatigue of muscles and nerves through electric stimulation by a weak d.c. electromotive force generated by a biogalvanic battery when the device is in contact with skin.

These ion permeating devices have proved more effective for the remedy of stiffness or pains than the above enumerated household treatment apparatus and methods.

A treatment apparatus aiming at formation of a biogalvanic battery like the above ion permeating devices was disclosed (e.g., Utility Model Laid-open Publication No. Sho 57-103743) which is of an external short-circuit type using a combination of different metals.

The ion permeating device developed by the present inventor is a skin-contact type apparatus in which semiconductor crystal and metal having a higher standard single electrode potential than the semiconductor crystal are electrically connected. This device is different both in its structure and effects, from the skin-contact type apparatus using a combination of different metals.

FIGS. 6A and 6B are diagrams illustrating differences between these two types of skin-contact type apparatus.

FIG. 6A illustrates a principle of a biogalvanic battery (cell) using a combination of a metal electrode 50 forming the positive pole of the cell and a semiconductor electrode 51 forming the negative pole of the cell. The metal electrode 50 and semiconductor electrode 51 are both in contact with the surface of a skin 52 at one side of each electrode, and are electrically shorted at another side of each electrode by a conductive member 53. The metal electrode 50 is made of metal having a standard single electrode potential higher than the semiconductor electrode 51. A closed circuit is formed by the skin 52, semiconductor electrode 51, conductive member 53, and metal electrode 50, and electrons start to flow from the semiconductor electrode 51 to the metal electrode 50 through the conductive member 53.

Electrons flowed from the semiconductor electrode 51 to the metal electrode 50 enter the electrolytic skin 52, and induce a reduction reaction (e.g., for iron ions in tissues, $Fe^{3+}+e^-\rightarrow Fe^{2+}$). At the same time, holes generated in the semiconductor electrode 51 with insufficient electrons drift by an internal electric field of a Schottky barrier generated at the skin contact surface and concentrate upon the skin contact surface of the semiconductor crystal to ionize atoms of the semiconductor electrode 51 at this surface. Since the internal electric field functions to move positive ions and holes out of the semiconductor electrode 51, and the dissociated semiconductor ions together with holes permeate through the skin. Holes in the skin 52 induce an oxidation reaction (e.g., $Fi^{3+}\leftarrow h^++Fe^{2+}$).

The Schottky barrier at the interface between the semiconductor electrode 51 and skin 52 functions to prevent both electrons and negative ions from flowing from the skin 52 into the semiconductor electrode 51. Accordingly, removal of positive ions and drainage of holes, thus the oxidation reaction reliably continues at the skin and an electromotive force is retained for a long period of time.

In the skin-contact type apparatus using a combination of different metals (e.g., Cu and Zn) shown in FIG. 6B, in place of the semiconductor electrode 51 shown in FIG. 6A, a metal electrode 54 forming the negative pole of the cell (e.g., Zn) is used which is made of metal having a smaller electron affinity x than the metal electrode 50 forming the positive pole of the cell (e.g., Cu), and the other structures are the same as FIG. 6A. Since electrons outflow from the metal electrode 54 through the conductive member 53 into the metal electrode 50 having a larger electron affinity x, the metal electrode 54 becomes short of electrons and must be charged positive. The metal electrode 54 does not form a Schottky barrier at the skin contact surface, water-derived negative ions $OH^-$ distributed at or near the skin surface enter the surface layer of the metal electrode 54 and are adsorbed and chemically reacted with the surface layer. As a result, the skin contact surface of the metal electrode 54 is covered with a hydroxide layer 55.

For example, with a combination of Cu and Zn, the following reaction occurs at the skin contact surface of the Zn metal electrode 54.

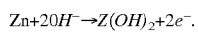

$$Zn+2OH^-\rightarrow Z(OH)_2+2e^-.$$

Such base metal hydroxide is generally insulative. The surface of the metal electrode 54 therefore increases its resistance and the electromotive force becomes unstable. As the hydroxide layer 55 becomes thicker, generation of electricity eventually stops. This is a surface passivation phenomenon.

Still further, with the combination of the metal electrode 50 and semiconductor electrode 51 shown in FIG. 6A, ions (e.g., $Fe^{2+}$) generated through reduction under the electrode 50 and ions (e.g., $Fe^{3+}$) generated through oxidation under the electrode 51 both diffuse in counter directions, as a result forming a net charge flow 55 of positive ions in the skin, from the semiconductor electrode 51 toward the metal electrode 50. These counter flows of the ions compensates for losses of ions caused by the reduction and oxidation reactions under the metal electrode 50 and semiconductor electrode 51, so that a so-called back electromotive force of a battery is hard to be generated.

In contrast, with the combination of different metals such as shown in FIG. 6B, the loss of ions (e.g., $Fe^{3+}$) which are used for generating ions (e.g., $Fe^{2+}$) through reduction under the metal electrode 50 cannot be compensated for from the region under the metal electrode 54. Therefore, the ions to be reduced gradually becomes insufficient in number and a back electromotive force is likely to be generated.

As described above, a biogalvanic battery of a metal positive pole - semiconductor negative pole type with an external short-circuit maintains a stable electromotive force after skin-contact because of stable reduction/oxidation reactions. Accordingly, the medical treatment apparatus for stiffness and pains has shown a high score of remedy results in practical use with less degradation even after a long period of skin-contact.

SUMMARY OF THE INVENTION

It is an object of the present invention to provide a skin-contact type medical treatment apparatus suitable for long term continuous use.

According to one aspect of the present invention, there is provided a skin-contact type medical treatment apparatus comprising: a first conductive member having a first skin-contact surface in contact with a first surface of skin when in use, the first skin-contact surface being made of metal or its alloy; a second conductive member having a second skin-contact surface in contact with a second surface of skin different from the first surface when in use together with the first conductive member, the second skin-contact surface being made of n-type semiconductor material having a standard single electrode potential higher than that of the first skin-contact surface; and a protective resistor having a resistance value in the range of from 0.1 to 50 MΩ for electrically connecting the first and second conductive members at an area different from the first and second skin-contact surfaces.

As the skin-contact surfaces of the first and second conductive members are made in contact with the surface of skin, a biogalvanic battery is formed because of a difference of standard electrode potential between the two types of materials constituting the skin-contact surfaces. An electrical close circuit is formed along a passage from the first conductive member, protective resistor, second conductive member, and skin to thereby flow current through the close circuit. This generates stimulations of electricity conduction so that stiffness or pains can be effectively alleviated.

As skin is physiologically activated by electricity conduction stimulations, the skin impedance lowers. The protective resistor inserted into the close circuit suppresses an excessive increase of current which is otherwise caused by the lowered skin impedance. Accordingly, skin troubles such as flushness and itching can be suppressed even during a long term use of the apparatus.

DETAILED DESCRIPTION OF THE PREFERRED EMBODIMENTS

First, phenomena discovered during treatments by using the skin-contact type medical treatment apparatus developed by the inventor and shown in FIG. 6a will be described.

A biogalvanic battery using the metal electrode 50 forming the positive pole of the cell and semiconductor electrode 51 forming the negative pole of the cell can generate a stable electromotive force and continuously apply electrical stimulation to muscle and nerve tissues so that stiffness or pains can be remedied effectively. The reason of chronic stiffness or pains is generally attributable to the way how each patient goes through each daily life. Therefore, even if temporary remedy effects are present, stiffness or pains may often return if a treatment is terminated. The biogalvanic battery is therefore desired to continue to operate for a long time for the long term treatment.

Figure 6A:
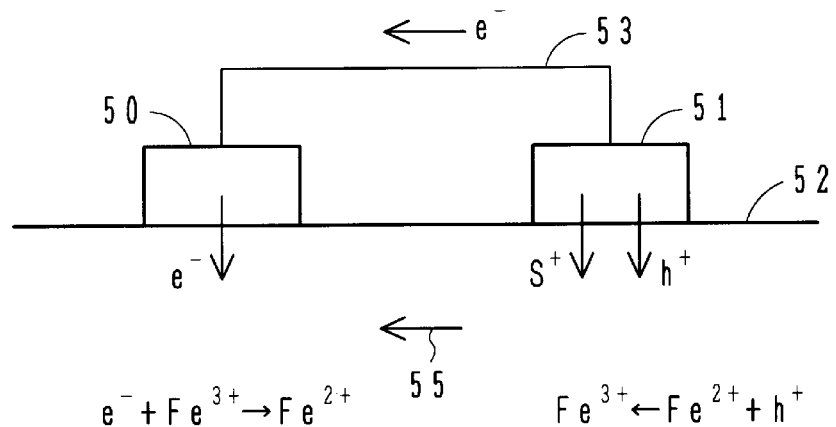
FIGS. 6A and 6B are diagrams illustrating the operation principles of conventional biogalvanic electricity generation, skin-contact type medical treatment apparatus.
Figure 6B:
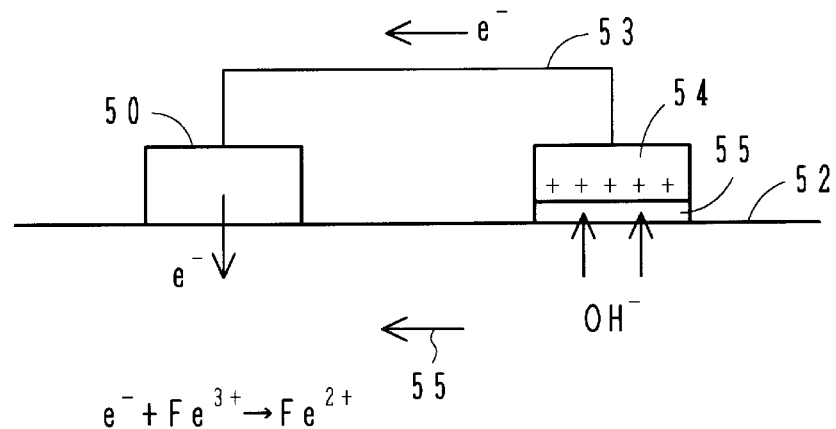

A theoretical electromotive force to be generated by the biogalvanic battery shown in FIG. 6A is determined by a combination of materials of the metal electrode 50 and semiconductor electrode 51 and a total chemical reaction energy of various oxidation (under the negative pole of the cell) and reduction (under the positive pole of the cell) reactions in the skin 52. Accordingly, the electromotive force or electric stimulation value can be adjusted by the combination of materials on the assumption that the same patient uses the skin-contact type apparatus at the same skin position.

Figure 7:
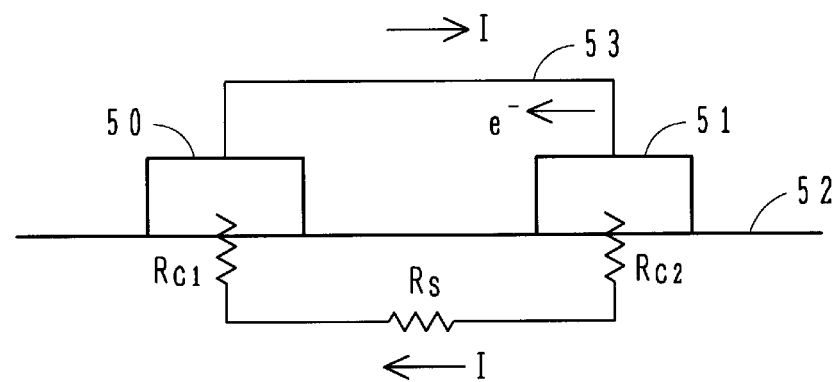
FIG. 7 is an equivalent circuit diagram of a conventional biogalvanic electricity generation, skin-contact type medical treatment apparatus.

Representing in voltage a theoretical electromotive force by ET and assuming a skin-contact closed circuit as shown in FIG. 7, then an external electromotive force which can be picked up across the metal electrode 50 and semiconductor electrode 51 is given by:

$$E = (R_{c1}+R_{c2}) \times I = E_T - R_s \times I \quad (1)$$

where $R_s$ is an impedance in skin between the electrodes, i.e., an internal resistance (hereinafter merely called a "skin impedance") of the biogalvanic battery, $R_{c1}$ and $R_{c2}$ are contact resistances between the skin 52 and respective electrodes 50 and 51, and I is a circuit current.

Remedy effects for stiffness and pains presumably result from current stimulation by a biogalvanic battery so that in order to ensure intensive remedy effects, the current is required to be set large.

The current I is given by:

$$I = E_T/(R_s+R_{c1}+R_{c2}) \quad (2)$$

where $R_{c2} \gg R_{c1}$ generally stands.

Elders generally have a low skin water content so that the total contact resistance $R_c$ (=$R_{c1}$+$R_{c2}$) and skin impedance $R_s$ are both high.

The skin impedance $R_s$ can be reduced by shortening the distance between the metal electrode 50 and semiconductor electrode 51. For elders and serious patients, it is therefore effective to set a material combination which gives a high theoretical electromotive force ET and to devise the device shape of a skin-contact type medical treatment apparatus (devising in order to reduce the skin impedance $R_s$ and the total contact resistance $R_c$).

The invivo skin impedance $R_s$ has a nature of changing it greatly.

The inventor has discovered by himself during experiments of biogalvanic batteries that the skin impedance $R_s$ lowers considerably when muscle or nerve tissues are physiologically activated by electricity conduction by a biogalvanic battery in a skin-contact state.

Generally, a skin impedance between two points spaced apart by 1 cm is 10 to 50 MΩ, and the total contact resistance $R_c$ of both the electrodes is 1 to 15 MΩ. It has been found that the skin impedance $R_s$ and total contact resistance $R_c$ at the skin-contact area of a patient with alleviated stiffness or pains lower by about 50 to 95% of those before alleviation. This is attributable to a local rise in ion conductivity of the skin 52 due to activated metabolism such as skin respiration.

Since the theoretical electromotive force $E_T$ does not change basically, physiological activation leads to an unexpected increase (increase by 2 to twentyfold) in the in-skin current I, as seen from the equation (2) above. Such a current increase may apply excessive stimulation to skin tissues. Therefore, a patient with weak skins is likely to suffer allergy and may have their skin flushed or feel itching. Some patients had light skin damages although stiffness or pains were remedied.

This problem can be solved simply by selecting a combination of positive and negative electrode materials having a small theoretical electromotive force $E_T$. However, with a combination generating a small theoretical electromotive force ET, the remedy effects through electricity conduction are limited and may be degraded for elders or serious patients.

An increase in in-skin current after a long term continuous use has been discovered by the inventor himself. Embodiments of the skin-contact type medical treatment apparatus are suitable for a long term continuous use and prevents a large current increase even during a long term continuous use.

Figure 4:
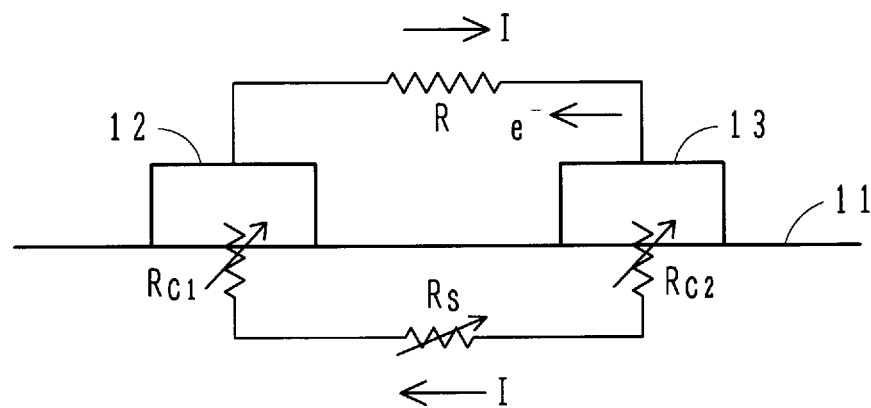
FIG. 4 is an equivalent circuit diagram of a skin-contact type medical treatment apparatus according to an embodiment of the invention.

FIG. 4 is an equivalent circuit of a skin-contact type medical treatment apparatus according to an embodiment of the invention. Electrodes 12 and 13 are made in contact with the surface of a skin 11 and connected together via a protective resistor R. The electrode 13 is made of material having a standard single electrode potential lower (electron affinity x smaller) than the material of the electrode 12. The contact resistance between the electrode 12 and skin 11 is represented by $R_{c1}$, the contact resistance between the electrode 13 and skin 11 is represented by $R_{c2}$, and the skin impedance is represented by $R_s$.

A closed circuit is formed by the skin 11, electrode 12, protective resistor R, and electrode 13, and current I flows through this closed circuit by a difference between standard electrode potentials of the electrodes 12 and 13. The current I is given by the following equations (3) and (4):

$$(R+R_{c1}+R_{c2}) \times I = E_T - R_s \times I \quad (3)$$

$$I = E_t/(R+R_s+R_{c1}+R_{c2}) \quad (4)$$

where the skin impedance $R_s$ and contact resistances $R_{c1}$ and $R_{c2}$ are variable, and generally $R_s \gg R_{c2} \gg R_{c1}$ stands.

If the protective resistance R is selected to be about the skin impedance $R_s$, then even if the skin impedance $R_s$ lowers by about one digit due to physiological activation, an increase in the current I can be suppressed as high as about a twofold at the most, as seen from the equation (4). It is therefore possible to prevent skin damages by conduction of excessive current.

Figure 5:
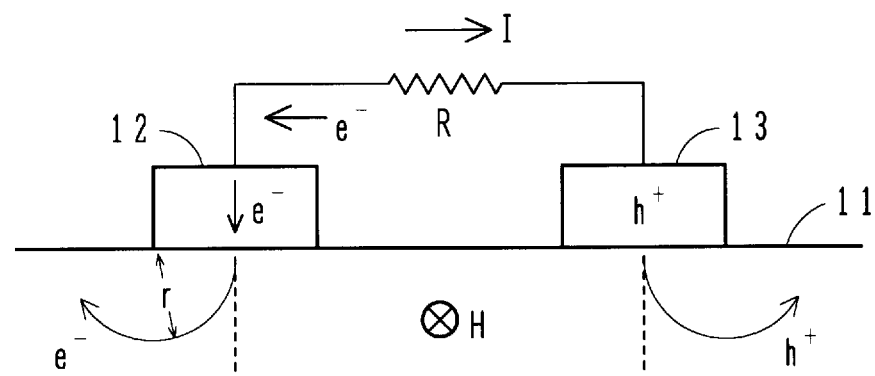
FIG. 5 is a diagram illustrating an operation principle of a skin-contact type medical treatment apparatus according to a modification of the embodiment.

FIG. 5 is a schematic diagram illustrating a motion of electrons and holes when the skin-contact type medical treatment apparatus shown in FIG. 4 is applied with a magnetic field H having an intensity sufficient for influencing the motion of electrons and holes injected into the skin.

Referring to FIG. 5, a magnetic field H of uniform intensity is applied to the skin near the electrodes 12 and 13 in the direction indicated in FIG. 5 (in the direction from the front to back of the drawing sheet). In this case, electrons e⁻ injected into the skin under the electrode 12 and holes h⁺ injected into the skin under the electrode 13 undergo an action of electromagnetic force and move circularly in the directions indicated in FIG. 5. The radius of this circular motion is in inverse proportion to the magnetic field intensity H and in proportion to the in-skin permeation speed and electron mass (or hole mass). This circular motion propagates the electron reduction reaction and hole oxidation reaction outward of the electrodes. Accordingly, local densities of ions generated through reduction and oxidation are lowered so that an inverse electromotive force (depolarization action) of the battery becomes difficult to be generated.

Next, various embodiments realizing the equivalent circuits shown in FIGS. 1 and 2 will be described.

Figure 1:
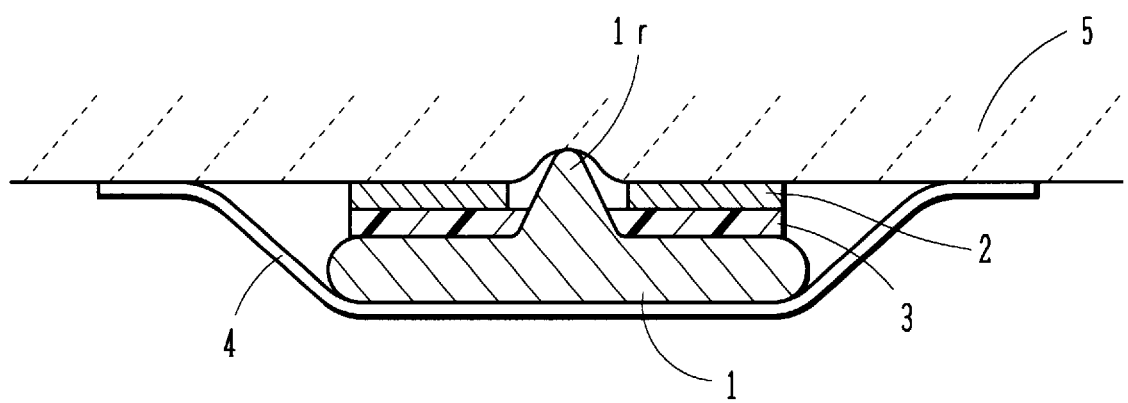
FIG. 1 is a cross sectional view of a skin-contact type medical treatment apparatus according to a first embodiment of the invention.

FIG. 1 is a cross sectional view of a skin-contact type medical treatment apparatus of the first embodiment in a skin-contact state. The skin-contact type medical treatment apparatus of the first embodiment is constituted by a electrode member 1 made of brass, an epoxy-containing resin film 3, a electrode member 2 made of zinc, and an adhesive tape 4.

The electrode member 1 is of a disk shape with a diameter of 6 mm and a thickness of 2 mm and has a projection 1r of 3 mm high at the central area thereof. Part or the whole of the surface of the electrode member 1 on the projection 1r side is plated with gold.

The electrode member 2 is of a ring shape having an outer diameter of 6 mm, an inner diameter of 2.5 mm, and a thickness of 1 mm, the surface thereof being formed with a zinc oxide film about 0.5 μm thick through acidification.

The epoxy containing resin film 3 is formed by coating epoxy containing resin which also contains carbon particles, on the flat surface with the projection 1r of the electrode member 1 to a thickness of about 1 mm. After the electrode member 2 is placed on the resin film 3 before the resin constituting the resin film 3 dries, the electrode member 2 and resin film 3 are bonded together by the resin.

The surface of the electrode member 1 opposite to the surface with the projection 1r is adhered to the adhesive surface of the adhesive tape 4. As the adhesive tape 4 covering the electrode member 1 is attached to the skin 5, the gold film plated on the tip of the projection 1r and the zinc oxide film formed on the surface of the electrode member 2 contact the surface of the skin 5.

The gold film on the tip of the projection 1r functions as the metal electrode 12 forming the positive pole of the cell shown in FIG. 4, the zinc oxide film on the surface of the electrode member 4 functions as the semiconductor electrode 13 forming the negative pole of the cell shown in FIG.

4, and the epoxy containing resin film 3 functions as the protective resistor R shown in FIG. 4.

A thickness of a high electric field region (a depletion layer region formed by a Schottky barrier) in the semiconductor region formed on the skin contact area of the electrode member 2 is generally 1 to 3 $\mu$m. Therefore, in the first embodiment, the zinc oxide film on the surface of the electrode member 2 is depleted over the whole thickness of the film. Electrons flow from the electrode member 2 to the electrode member 1, and holes formed in the zinc oxide film on the surface of the electrode member 2 are injected very fast into the skin by the internal electric field generated in the depletion layer.

As different from the skin-contact type medical treatment apparatus shown in FIG. 6A, an ion bonding force between zinc and oxygen atoms of zinc oxide is strong, so that semiconductor ions in the electrode member 2 are not injected into the skin. Rather, since electrons are outflowed, the electrode member 2 becomes chemically active and the oxidation reaction between zinc and zinc oxide film at the interface therebetween is enhanced. As a result, the zinc oxide film rapidly thickens to 1 to 3 $\mu$m which is the thickness of the expected high electric field region. Oxidation at the interface gradually progresses thereafter so that it is supposed that semiconductor ions hardly move out of the skin contact surface, as opposed to covalent semiconductor.

The resistance value of the protective resistor R between the projection 1r and electrode member 2 measured before skin contact was about 10 M$\Omega$.

The treatment results of the first embodiment will be described.

The efficacy was investigated by tightly attaching, with adhesive tapes, skin-contact type medical treatment apparatus of the first embodiment to the skins 5 of patients having pains in shoulders. Treatments were performed by attaching three skin-contact type medical treatment apparatus per one patient for three days. The treatment results, including very effective persons, effective persons, ineffective persons, and skin damaged persons among 75 male and female inspected persons.

Table of Treatment Results

|        | Ages | No. of Very Effective Persons | No. of Effective Persons | No. of Ineffective Persons | No. of Skin Troubled Persons |
|--------|------|---|---|---|---|
| Male   | 50   | 12 | 10 | 1 | 1 |
|        | 40   | 3  | 3  | 3 | 1 |
|        | 30   | 3  | 1  | 0 | 0 |
|        | 20   | 0  | 3  | 2 | 0 |
|        | Sub-total | 18 | 17 | 6 | 2 |
| Female | 50   | 8  | 4  | 2 | 1 |
|        | 40   | 2  | 6  | 0 | 0 |
|        | 30   | 2  | 2  | 2 | 2 |
|        | 20   | 1  | 2  | 3 | 0 |
|        | Sub-total | 13 | 14 | 7 | 3 |
|        | Total | 31 | 31 | 13 | 5 |

As seen from Table, the effective treatment percentage, i.e., a value of the sum of very effective and effective persons divided by the total number of inspected persons, was 82.7%. The percentage of skin troubled persons such as flushness or itching of skin was 6.7%.

First comparison examples for comparing with the treatment results of the first embodiment will be described.

For the comparison with the first embodiment, the electrode member 1 and electrode member 2 shown in FIG. 2 were directly adhered with conductive paste without interposing the epoxy containing resin film 3 (i.e., with the external circuit being almost short-circuited), and similar treatment tests were conducted.

The effective treatment percentage of the comparison examples was about 85% slightly higher than the first embodiment. However, the number of skin troubles increased to about 17%.

The skin troubles shown in Table 1 although not so many were inspected in detail. Most of these skin troubles were apparently light contact type dermatitis, and troubles near the electrode by electricity conduction was less. In contrast, more than a half (70% or more of inspected persons) of skin troubles of the first comparison examples were recognized as caused by electricity conduction.

In the first embodiment, incorporation of the resin film 3 functioning as the protective resistor enabled to reduce the skin troubles by electricity conduction by about ¼ to ⅕ as compared to not using the resin film. Although the electromotive force appearing at the skin contact area of the skin-contact type medical treatment apparatus is 0.6 to 1.2 V, it can be considered that the resistance value R of the resin film 3, e.g., about 10 M$\Omega$ (approximately corresponding to the skin impedance at the start of skin contact) suppresses the generation of excessive current after physiological activation.

Figure 2A:
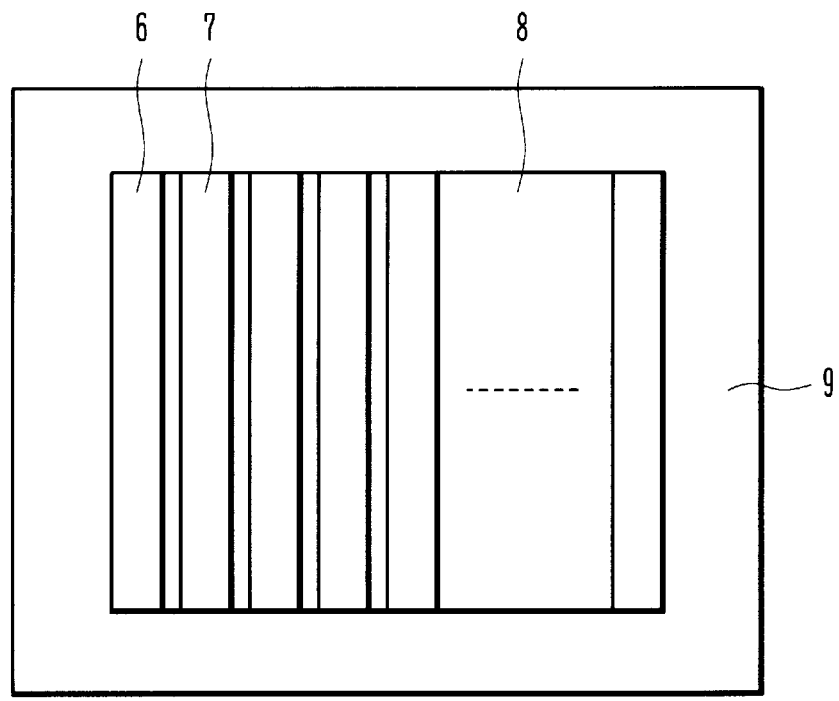
FIGS. 2A and 2B are a plan view and a side view of a skin-contact type medical treatment apparatus according to a second embodiment of the invention.
Figure 2B:
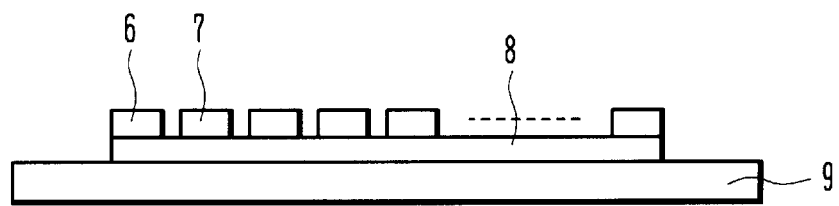

FIGS. 2A and 2B show the structure of a skin-contact type medical treatment apparatus of the second embodiment, FIG. 2A is a plan view of the apparatus, and FIG. 2B is a side view thereof.

A polyimide film 8 is adhered to the area other than a peripheral adhesive surface of an adhesive cloth 9. For example, the size of the adhesive cloth 9 is 50×50 mm$^2$, and the thickness of the polyimide film 8 is about 0.5 mm. The peripheral adhesive surface is adhered to skin. Indium oxide ($In_2O_3$) is dispersed and contained in the polyimide film 8.

Electrode members 6 and electrode members 7 respectively made of oblong films regularly spaced are alternately disposed on the surface of the polyimide film 8 in a stripe pattern. For example, the widths of the electrode members 6 and 7 are 2 mm, and the distance between adjacent electrode members 6 and 7 is 1 mm. The electrode members 6 and 7 are attached to the surface of the polyimide film 8 before the monomer source material of the polyimide film 8 is polymerized, to thereafter adhere to the polyimide film 8 because the monomer source material is polymerized into the polyimide film.

The electrode member 6, forming the positive pole of the cell, is made of a tin stripe film on the surface of which a rhodium film of 2 $\mu$m thick is covered. The electrode member 7, forming the negative pole of the cell, is made of a tin stripe film on the surface of which a tin oxide thin film is vapor deposited to about 0.5 $\mu$m thick.

The rhodium film plated on the surface of the electrode member 6 functions as the metal electrode 12 shown in FIG. 4, the tin oxide thin film vapor deposited on the surface of the electrode member 7 functions as the semiconductor electrode 13 shown in FIG. 4, and the polyimide film 8 functions as the protective resistor R. The resistance value of the protective resistor R with the structure shown in FIGS. 2A and 2B is, for example, about 0.5 M$\Omega$.

The treatment results of the second embodiment will be described.

The skin-contact type medical treatment apparatus is attached to a diseased area of stiffness or pains by adhering the peripheral adhesive area of the adhesive cloth 9 to the skin. In this state, an electrically closed circuit is formed along a passage of electrode member 7 covered with an n-type tin oxide thin film→polyimide film 8 4 electrode member 6 covered with a rhodium film→skin→electrode member 7. Therefore, a biogalvanic battery generates electricity to apply stimulation of electricity conduction to subcutaneous tissues.

In the second embodiment, the electromotive force appearing at the skin contact area is 0.3 to 0.7 V considerably lower than the first embodiment. Therefore, even if the resistance value of the protective resistor R was lower by one digit than the first embodiment, skin troubles by treatments was confirmed to be about 5% of all inspected patients.

Since the skin-contact type medical treatment apparatus of the second embodiment is broad and flexible, it features that a single sheet of apparatus can cover a broad diseased area. The effective treatment percentage of this skin-contact type medical treatment apparatus applied to patients having pains in waists was in excess of 70%.

Second comparison examples for comparing with the treatment results of the second embodiment will be described.

For the comparison with the second embodiment, the polyimide film 8 shown in FIGS. 2A and 2B was removed and electrode members 6 and 7 were attached with conductive paste to the place where the polyimide film was formed. This led to direct electrical connection between 6 and 7. With this apparatus, the second comparison examples were obtained.

With treatments by this apparatus, the skin troubles increased to 20% of inspected patients.

In the second embodiment, incorporation of the polyimide film 8 functioning as the protective resistor enabled to reduce the skin troubles by electricity conduction by about ¼ as compared to not using the polyimide film.

Figure 3:
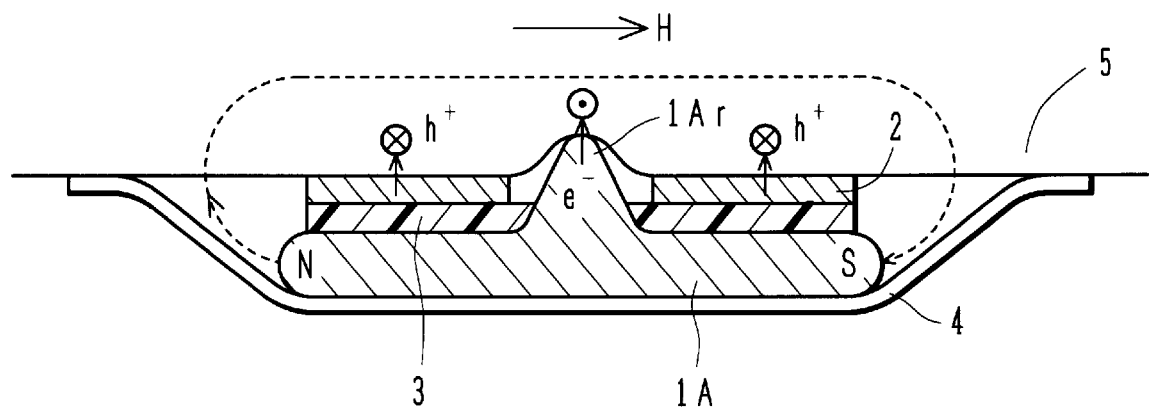
FIG. 3 is a cross sectional view of a skin-contact type medical treatment apparatus according to a third embodiment of the invention.

FIG. 3 is a cross sectional view of a skin-contact type medical treatment apparatus of the third embodiment.

The skin-contact type medical treatment apparatus of the third embodiment uses an electrode member 1A made of sintered ferrite in place of the electrode member 1 made of brass of the apparatus shown in FIG. 1. Similar to FIG. 1, a projection 1Ar is formed on one surface of the electrode member 1A. Gold (18K) is plated to a thickness of about 3 $\mu$m on the surface with the projection 1Ar of the electrode member 1A. The other structures are the same as the apparatus shown in FIG. 1.

The electrode member 1A is magnetized in the radial direction, with a pair of magnetic poles being formed at opposing circumferential areas. The magnetic flux density near a magnetic pole is about 1200 gausses.

As this skin-contact type medical treatment apparatus is made in contact with skin, a biogalvanic battery is formed having a gold film plated on the tip surface of the projection 1Ar as its metal electrode functioning the positive pole of the cell and a zinc oxide thin film formed on the surface of the electrode member 2 as its semiconductor electrode functioning the negative pole of the cell. A magnetic field H is applied to the inside of the skin 5 in the direction from the N pole to S pole of the electrode member 1A (in the direction from left to right as viewed in FIG. 3).

The magnetic flux density of 1200 gausses supplies a magnetic field intensity sufficiently large for applying an electromagnetic force, to electrons $e^-$ injected into the skin 5 from the gold film (18K) of the metal electrode of the biogalvanic battery, and to holes $h^+$ injected into the skin 5 from the n-type zinc oxide film of the semiconductor electrode of the battery.

Therefore, electrons injected from the metal electrode in a skin-contact state move circularly from the back of the drawing sheet to the front thereof as shown in FIG. 3, whereas the holes injected from the semiconductor electrode move circularly in the opposite direction. A carrier concentration under the metal and semiconductor electrodes lowers therefore and the oxidation/reduction area correspondingly expands outward of the electrodes. Accordingly, polarization by oxidized and reduced ions accumulated under the electrodes becomes small so that the electromotive force can be advantageously prevented from being lowered by a long time skin contact.

The treatment results of the third embodiment will be described.

Treatments were conducted for a number of male and female persons (75 persons in total) at each generation having stiffness in their shoulders, by using skin-contact type medical treatment apparatus of the third embodiment. Similar to the first embodiment, three apparatus per each person were attached for three days. The effective treatment percentage was calculated by dividing the sum of very effective and effective persons by the total number of inspected persons.

The effective treatment percentage was about 89%. The skin troubles was at a low level of about 5% similar to the second embodiment. The reason of a higher effective treatment percentage than the first embodiment may be attributable to an efficacy of applied magnetic field. Physical stimulations remedying stiffness or pains are supposedly a multiplication of acupuncture point pressure efficacy (finger pressing efficacy), electricity conduction efficacy, and magnetic field efficacy.

For the comparison among these of efficacy, the same persons having stiffness in shoulders were treated with commercially available magnetic treatment apparatus (magnetic flux density of 1200 gausses). Also in this case, the treatment results were inspected under the same conditions of three apparatus per one person and three-day attachment. The effective treatment percentage was about 37%.

Assuming that the remedy is achieved by a simple coupling of the three physical stimulations, a contribution of each physical stimulation to the treatment results is 34.5% for finger pressing, 58.4% for electricity conduction, and 7.1% for magnetic field, according to the above treatment data.

In the first and third embodiments shown in FIGS. 1 and 3, the positive pole of the cell is a gold film plated on the tip of the projection formed on one surface of the electrode member made of conductive material. The negative pole of the cell is an oxide semiconductor thin film formed on the surface of the electrode member adhered to the resin film on the flat surface of the positive pole of the cell on the projection side. In generalizing the shape of the positive pole having a projection, the positive pole of the cell may be constituted by a skin-contact portion and a conductive portion wherein a step is formed between a skin-contact surface of the skin-contact portion and the surface of the conductive portion continuous with the skin-contact surface. In this generalized case, the conductive portion of a positive pole of the cell, a resin film functioning as the protective resistor, and a negative pole of the cell having an oxide semiconductor thin film on the surface thereof are stacked in this order and mechanically and electrically coupled together.

The structures of the positive and negative poles of the cell may be reversed. Specifically, the negative pole of the cell may be constituted by a skin-contact portion and a conductive portion wherein a step is formed between a skin-contact surface of the skin-contact portion and the surface of the conductive portion continuous with the skin-contact surface. The positive pole of the cell is adhered to the resin film formed on the surface of the conductive portion of the negative pole of the cell. The skin-contact surface of the negative pole is formed with, for example, a zinc oxide thin film, and the surface of the positive pole is formed with, for example, a gold film.

In the first to third embodiments, since a protective resistor is loaded into an external circuit of a biogalvanic battery, skin troubles such as flushness or itching can be suppressed which might otherwise be caused by a rapid fall of a skin impedance during treatment of stiffness or pains. A combination of materials of the positive and negative poles of the cell generating a high electromotive force is therefore possible and stiffness or pains can be remedied more effectively.

The negative pole covered with an oxide semiconductor thin film is formed through acidification of the metal surface. Therefore, a skin-contact type medical treatment apparatus which is disposable and inexpensive can be provided.

Next, modifications of the first to third embodiments will be described.

At least the skin-contact surface of the electrode member forming the positive pole of the cell may use, in addition to gold (Au), gold alloy, and rhodium (Rh) used in the first to third embodiments, platinum (Pt), iridium (Ir), palladium (Pd), silver (Ag), and alloy of these.

Although a metal having a high standard electrode potential such as copper (Cu) may be theoretically used other than noble metals, it is easy to be oxidized and is not durable for a long term use.

As the skin-contact surface of the electrode member functioning to the negative pole of the cell, oxide semiconductors other than zinc oxide (ZnO) and tin oxide (SnO) used in the first to third embodiments, such as indium oxide ($In_2O_3$), bismuth oxide ($Bi_2O_3$), and oxygen deficient aluminum oxide ($Al_2O_{3-x}$) may be used. Non-oxidizing n-type semiconductors, such as n-type Ge and n-type SiC may also be used.

Instead of a conductive filler dispersion resin film serving as the protective resistor, a conductive high polymer layer or an inorganic resistor may be used. Material whose resistance varies with a voltage applied across both ends may be used. For example, conductive liquid crystal sandwiched between electrode panels may be used. With such a variable resistor, its resistance value can be made large as the voltage of a biogalvanic battery appearing at the external circuit rises when subcutaneous tissues are physiologically activated by the operation of the battery and the skin impedance $R_s$ or the sum $R_c$ of contact resistances rapidly lower. While the subcutaneous tissues are inactive (stiffness or pains still existing), the variable resistor lowers its resistance and allows a large current to flow, whereas while the stiffness or pains are alleviated, it raises its resistance to suppress a current flow. Therefore, this variable resistor is more preferable as the protective resistor.

Although a proper resistance value R of a protective resistor depends upon a combination of positive and negative pole materials, it may be selected in the range of from 0.1 to 50 MΩ. This range has been empirically determined from the range of skin impedance and skin-contact treatment data.

The present invention has been described in connection with the preferred embodiments. The invention is not limited only to the above embodiments. It is apparent to those skilled in the art that various modifications, improvements, combinations and the like can be made without departing from the scope of the appended claims.

I claim:

1. A skin-contact type medical treatment apparatus comprising:
   a first conductive member having a first skin-contact surface adapted to be in contact with a first surface of skin when in use, the first skin-contact surface being made of metal or its alloy;
   a second conductive member having a second skin-contact surface adapted to be in contact with a second surface of skin different from the first surface when in use together with the first conductive member, the second skin-contact surface being made of n-type semiconductor material having a standard single electrode potential lower than that of the first skin-contact surface; and
   a protective resistor having a resistance value in the range of from 0.1 to 50MΩ for electrically connecting the first and second conductive members at an area different from the first and second skin-contact surfaces.

2. A skin-contact type medical treatment apparatus according to claim 1, wherein the first skin-contact surface of the first conductive member is made of noble metal or its alloy.

3. A skin-contact type medical treatment apparatus according to claim 2, wherein one of the first and second conductive members includes a skin-contact portion having the skin-contact surface and a conductive portion having a surface continuous with the skin-contact surface, a step is formed between the skin-contact surface and the surface of the conductive portion, and the resin film, the other of the first and second conductive members are stacked in this order on the surface of the conductive portion.

4. A skin-contact type medical treatment apparatus according to claim 3, wherein the skin-contact portion is a projection formed on the surface of the conductive portion.

5. A skin-contact type medical treatment apparatus according to claim 4, wherein the resin film is disposed on the surface of the conductive portion, surrounding the projection, and the other of the first and second conductive members is of a disk shape having a through hole, and the other of the first and second conductive members is disposed with the projection being inserted into the through hole.

6. A skin-contact type medical treatment apparatus according to claim 2, wherein the first and second conductive members are made of a plurality of oblong films, and the first and second conductive members are attached to the surface of the resin film, being disposed alternately.

7. A skin-contact type medical treatment apparatus according to claim 1, wherein the protective resistor is a resin film containing conductive filler dispersed therein, and the first and second conductive members are electrically connected together by the resin film.

8. A skin-contact type medical treatment apparatus according to claim 7, wherein the conductive filler is carbon particles or indium oxide particles.

9. A skin-contact type medical treatment apparatus according to claim 1, wherein the second conductive member includes a surface layer constituting the second skin-contact surface and an internal member having the surface layer on the surface of the internal member, the surface layer is made of oxide semiconductor, and the inner member contains metal elements constituting the surface layer.

10. A skin-contact type medical treatment apparatus according to claim 1, further comprising a magnetic field generating member for generating a magnetic field in skin near the first and second skin-contact surfaces in a skin contact state.

11. A skin-contact type medical treatment apparatus according to claim 10, wherein at least one of the first and second conductive members is made of magnetized ferromagnetic material and also serves as the magnetic field generating member.

12. A skin-contact type medical treatment apparatus according to claim 1, wherein the first skin-contact surface of the first conductive member is made of one material selected from the group consisting of Au, Rh, Pt, Ir, Pd, Ag, and alloy of these noble metals.

13. A skin-contact type medical treatment apparatus according to claim 1, wherein the second skin-contact surface of the second conductive member is made of one material selected from the group consisting of zinc oxide, tin oxide, indium oxide, bismuth oxide, and oxygen deficient aluminum oxide.

* * * * *